United States Patent [19]

Masaki et al.

[11] Patent Number: 4,764,617

[45] Date of Patent: Aug. 16, 1988

[54] QUINALDINAMIDE DERIVATIVES

[75] Inventors: Mitsuo Masaki, Chiba; Haruhiko Shinozaki, Oomiya; Masaru Satoh, Koshigaya; Naoya Moritoh, Kuki; Koichi Hashimoto, Tokyo; Toshiro Kamishiro, Misato, all of Japan

[73] Assignee: Nippon Chemiphar Co., Ltd., Japan

[21] Appl. No.: 895,938

[22] Filed: Aug. 13, 1986

[51] Int. Cl.[4] .................. C07D 215/48; C07D 401/06
[52] U.S. Cl. ................... 546/169; 540/596; 514/906
[58] Field of Search ............... 546/169; 514/311, 317; 540/596

[56] References Cited

U.S. PATENT DOCUMENTS 1,825,623  9/1931  Miescher ........................ 546/169
3,932,416  1/1976  Bays et al. ..................... 546/169

Primary Examiner—Glennon H. Hollrah
Assistant Examiner—D. B. Springer
Attorney, Agent, or Firm—Gerald J. Ferguson, Jr.

[57] ABSTRACT

A novel quinaldinamide derivative having the formula:

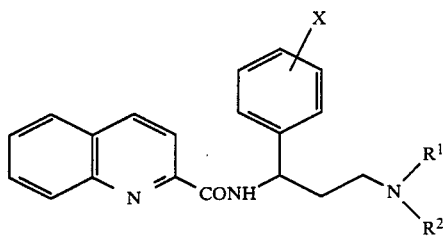

wherein each of $R^1$ and $R^2$ independently represents a lower alkyl group or $R^1$ and $R^2$ are combined together with the adjacent nitrogen atom to form a 5-7 membered ring; and X represents the hydrogen atom, a lower alkyl group or a lower alkoxy group, and its acid-addition salt, which show prominent central muscle relaxant effect, namely rigidity relieving effect on anemic decerebrated rigidity.

8 Claims, 1 Drawing Sheet

QUINALDINAMIDE DERIVATIVES

BACKGROUND OF THE INVENTION

1. Field of the Invention

The present invention relates to a novel quinaldinamide derivative and a process for the preparation of the same.

2. Description of the Prior Arts

As a quinaldinamide derivatives, N-(2-diethylaminoethyl)quinaldinamide is described in Ger. Offen. No. 2,009,894; M. Giannini, P. Boni, M. Fedi, G. Bonacchi, Farmaco, Ed. Sci., 28, 429-47 (1973); and P. Boni, C. Bacciarelli, Farmaco, Ed. Sci., 29, 923-35(1974). These publications are silent with respect to rigidity relieving effect of the described quinaldinamide compound. It has been experimentally confirmed by the present inventors that this quinaldinamide derivative shows very weak rigidity relieving effect.

SUMMARY OF THE INVENTION

It is an object of the present invention to provide a novel quinaldinamide derivative showing a marked central muscle relaxant effect, namely, marked rigidity relieving effect on anemic decerebrated rigidity.

It is another object of the invention to provide a novel quinaldinamide derivative of value as a pharmaceutical.

It is a further object of the invention to provide a novel quinaldinamide derivative of value as an insecticide.

It is a further object of the invention to provide a process for the preparation of the novel quinaldinamide derivative.

There is provided by the present invention a quinaldinamide derivative having the formula (I):

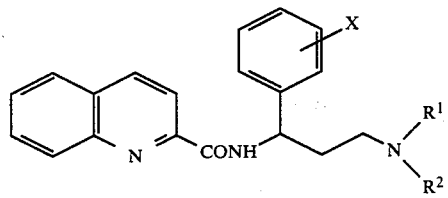

wherein
each of $R^1$ and $R^2$ independently represents a lower alkyl group containing, for instance, 1-6 carbon atoms, or $R^1$ and $R^2$ are combined together with the adjacent nitrogen atom to form a 5-7 membered ring; and X represents the hydrogen atom, a lower alkyl group containing, for instance, 1-6 carbon atoms or a lower alkoxy group containing, for instance, 1-6 carbon atoms, and its acid-addition salt.

DETAILED DESCRIPTION OF THE INVENTION

Figure 1:
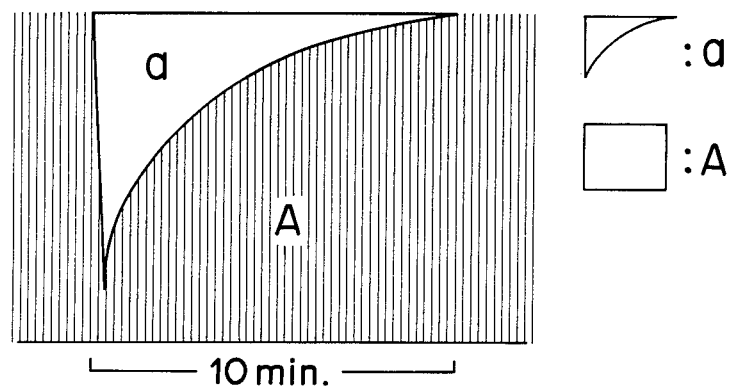
FIG. 1 shows a figure to be employed for calculation of rigidity relieving effect of the compounds.

The quinaldinamide derivative of the formula (I) shows a prominent central muscle relaxant effect, namely, marked rigidity relieving effect on anemic decerebrated rigidity.

The quinaldinamide derivative of the formula (I) according to the present invention can be prepared by a reaction between quinaldinic acid of the formula (II):

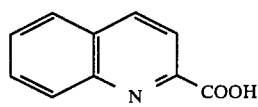

or its reactive derivative and a compound of the formula (III):

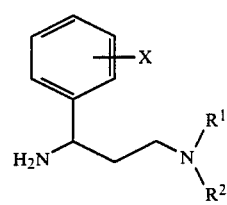

wherein $R^1$, $R^2$ and X have the same meanings as mentioned above.

Examples of the reactive derivatives of the quinaldinic acids include acid halides such as acid chloride and acid bromide, mixed acid anhydrides such as that derived from a combination of quinaldinic acid and monoalkylcarbonic acid, said anhydrides of quinaldinic acid, and active esters such as p-nitrophenylester of quinaldinic acid.

Accordingly, the quinaldinamide derivative of the formula (I) can be prepared by any one of known processes for the formation of an amide-bonding through condensation reaction, for instance:

(1) an acid halide process using a quinaldinoyl halide such as quinaldinoyl chloride or quinaldinoyl bromide;

(2) a process of causing reaction of the starting compounds in the presence of a condensation agent such as N,N'-dicyclohexylcarbodiimide, a combination of N,N'-dicyclohexylcarbodiimide and N-hydroxysuccinimide or a combination of N,N'-dicyclohexylcarbodiimide and 1-hydroxybenzotriazole;

(3) a mixed acid anhydride process using, for example, an acid anhydride derived from a combination of quinaldinic acid and monoalkylcarbonic acid;

(4) an acid anhydride process using, for example, acid anhydride of quinaldinic acid;

(5) an active ester process using, for example, p-nitrophenylester of quinaldinic acid; and (6) a process of heating the starting compounds in the absence of a condensation agent.

The reaction between quinaldinic acid or quinaldinoyl halide and a compound of the formula (II) can be performed according to the following reaction equation:

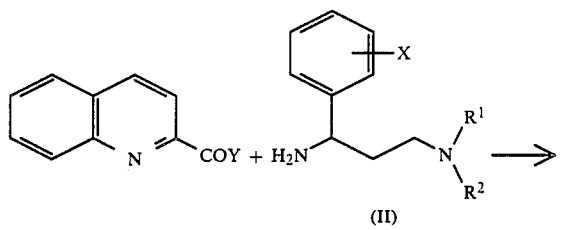

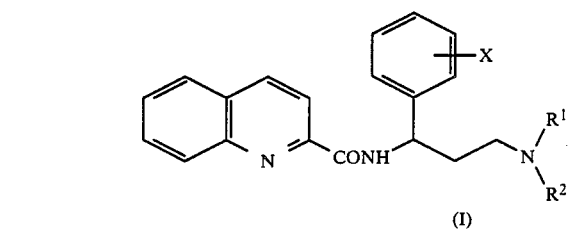

wherein Y represents a halogen atom or a hydroxyl group, and $R^1$, $R^2$ and X have the same meanings as mentioned above.

The reactions can be performed with no solvent or in an organic solvent being inert to the reactions, such as methylene chloride, chloroform, ether, tetrahydrofuran, benzene, or ethyl acetate.

The quinaldinamide derivative obtained in the above reactions can be converted to an acid-addition salt (i.e. salt with an acid) by a known method. Examples of the acids employable for the formation of the acid-addition salt include hydrochloric acid, hydrobromic acid, sulfuric acid, phosphoric acid, citric acid, fumaric acid, maleic acid, tartaric acid, oxalic acid, methanesulfonic acid and p-toluenesulfonic acid.

The starting compound of the formula (II) can be prepared, for instance, by the process according to the following equation:

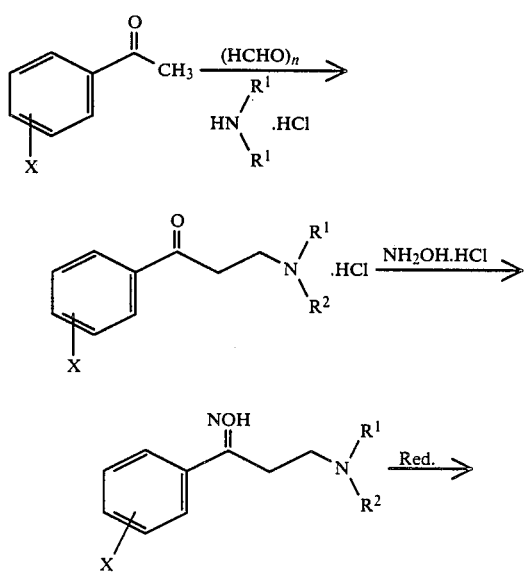

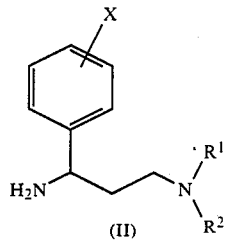

Representative examples of the compounds of the formula (I) according to the invention include:

Compound 1: N-(3-dimethylamino-1-phenylpropyl)-quinaldinamide;

Compound 2: N-(3-diethylamino-1-phenylpropyl)-quinaldinamide;

Compound 3: N-(1-phenyl-3-dipropylaminopropyl)-quinaldinamide;

Compound 4: N-(1-phenyl-3-pyrrolidinopropyl)quinaldinamide;

Compound 5: N-(1-phenyl-3-piperidinopropyl)quinaldinamide;

Compound 6: N-[3-(perhydroazepin-1-yl)-1-phenylpropyl]quinaldinamide;

Compound 7: N-[1-(2-methylphenyl)-3-piperidinopropyl]quinaldinamide;

Compound 8: N-[1-(3-methylphenyl)-3-piperidinopropyl]quinaldinamide;

Compound 9: N-[1-(4-methylphenyl)-3-piperidinopropyl]quinaldinamide; and

Compound 10: N-[1-(4-methoxyphenyl)-3-piperidinopropyl]quinaldinamide.

Experimental results of the central muscle relaxant effect (i.e., rigidity relieving effect on anemic decerebrated rigidity) and toxicity of the compounds of the formula (I) according to the invention are given below.

In the description of the experimental results, control compounds are as follows:

Control Compound 1: N-(2-diethylaminoethyl)quiinaldinamide fumarate; and

Control Compound 2: tolperisone by hydrochloride (2,4'-dimethyl-3-piperidinopropiophenone hydrochloride, known muscle relaxant)

EXPERIMENT 1

Effect on Anemic Decerebrated Rigidity

The experiment was performed using specimen of anemic decerebrated rigidity produced in rats according to the method of Fukuda, H., Ito, T., Hashimoto, S., and Kudo, Y.; Japan, J., Pharmacol., 24, 810 (1974).

Wister male rats (body weight: 270 to 350 g) were held on their backs and incised at their cervices under etherization. After the trachea and common carotid arteries were exposed, the trachea was cannulated and the bilateral common carotid arteries and esophagus were then double-litigated and cut. Subsequently, its occipital bone was exposed through which a circular hole was bored to double-ligate the centrally extending basilar artery. As each rat started coming out of anesthetization, its front limbs became rigid.

Measurement was conducted by recording electromyographic (EMG) response from the muscle of the forelimb (M. triceps brachii) of the rat in the rigid state. The EMG pulses were converted to accumulated values every 10 seconds and recorded as a histogram on a recorder.

The effect of each test compound on the rigidity was evaluated in terms of the suppression rate. This rate was calculated first by determining the area (see FIG. 1) of a decreased EMG pulse part on the histrograpm upon passage of 10 minutes after administration of a physiological saline solution of each test compound (3 mg/kg) through the femoral vein and then in accordance with the following equation:

Suppression rate $(\%) = (a/A) \times 100$ wherein a means an EMG pulse area decreased as a result of the administration of the test compound; and A means an EMG pulse area observed when no test compound was administered (control).

The results are set forth in Table 1.

TABLE 1

| Test Compound | Relieving Rate (%) |
| --- | --- |
| Compound 2* | 24.6 |
| Compound 4** | 19.6 |
| Compound 5* | 18.8 |
| Compound 6** | 12.2 |
| Compound 7* | 11.2 |
| Compound 8* | 11.7 |
| Control Compound 1 | 1.2 |
| Control Compound 2 | 4.8 |

Remarks:
Compounds 2, 4, 5, 6, 7 and 8 are those identified hereinbefore.
*means that the compound is in the form of fumarate, and **means that the compound is in the form of oxalate.

EXPERIMENT 2

Accute Toxicity $LD_{50}$ was determined by a known up-and-down method using ddN male mouse. The test compound was dissolved in a physiological saline solution, and the resulting solution was administered into the mouse through the tail vein.

The results are set forth in Table 2.

TABLE 2

| (Accute Toxicity Value) | |
| --- | --- |
| Test Compound | $LD_{50}$ (mg/kg) (iv) |
| Compound 2* | 18.9 |
| Compound 4** | 17.2 |
| Compound 5* | 24.8 |
| Compound 6** | 15.2 |
| Compound 7* | 23.5 |
| Compound 8* | 25.4 |

Remarks:
Compounds 2, 4, 5, 6, 7 and 8 are those identified hereinbefore.
*means that the compound is in the form of fumarate, and **means that the compound is in the form of oxalate.

The results given above indicate that the quinaldinamide derivative of the formula (I) are useful for the therapy of a complaint which would have spastic paralysis and rigidity and accordingly are useful for suppressing or releasing dyskinasis, athetosis, myoclonus, tic, tremors, dystonia and ballismus of neuropathy.

The quinaldinamide derivative of the formula (I) according to the invention can be administered orally or parenterally. Examples of the preparation forms for oral administration include tablets, capsules, powder, granules and syrup. Examples of the preparation forms for parenteral administration include an injectable preparation. For the formulation of the preparations, known additives such as excipients, disintegrants, binders, lublicants, pigments and diluents like can be employed. Examples of the excipients include dextrose and lactose. Examples of the disintegrants include starch and carboxymethylcellulose. Examples of the lubricants include magnesium stearate and talc. Examples of the binders include hydroxypropylcellulose, gelatin and polyvinylpyrrolidone.

The dose generally is from about 1 mg/day to about 50 mg/day in the case of an injectable preparation and from about 10 mg/day to about 500 mg/day in the case of oral administration, both for an adult. The dose may be either increased or decreased depending on the age and other conditions.

It has been further observed by the present inventors that the quinaldinamide derivative of the formula (I) shows prominent glutamic acid (or glutamate)-blocking effect. As has been strongly suggested in the prior art, glutamic acid acts as an excitatory neurotransmitter at the central nervous systems of higher animals and at the neuromuscular junctions of lower animals ["Glutamate as a Neuro-transmitter" edited by G. D. Chiara & G. L. Gessa: Raven Press, New York, 1981 and H. M. Gerschenfeld: Physiol. Rev., 53, 1–119 (1973)].

Therefore, the quinaldinamide derivative of the formula (I) capable of blocking glutamic acid is effective in agricultural use to reduce and weaken activities of insects, and is of value as an insecticide.

EXPERIMENT 3

Blocking Effects on Glutamic Acid at Neuromuscular Junctions of Crayfish

The method of Ishida et al., [(J. Physiol., 298, 301–319 (1980)] and that of Shinozaki et al. [Comp. Biochem. Physiol., 70c, 49–58 (1981)] were followed. The opener muscles of the first walking legs of crayfish were used as experimental materials. The neuromuscular sample was held in a bath in which a physiologicl solution [NaCl (195 mM), $CaCl_2$ (18 mM), KCl (5.4 mM), tris-maleate buffer (pH 7.5, 10 mM), and glucose (11 mM)] for use with the cray fish was perfused at room temperature and at a constant flow rate. A glass micro-electrode filled with a 3M-KCl solution was inserted in a central part of the muscle fiber to intracellularly record the changes in the potential of the muscular cell membrane.

The blocking effect of each test compound on glutamic acid was evaluated in terms of the suppression rate to depolarization which was induced by bath-applying L-glutamic acid ($10^{-4}$M) in a 5-minute pre-treatment with a solution of the test compound ($2 \times 10^{-4}$M). The results are shown in Table 3.

TABLE 3

| Test Compound | Glutamic Acid-Blocking Rate (%) |
| --- | --- |
| Compound 5 (of the invention) (N—(1-phenyl-3-piperidinopropyl)quinaldinamide) | 66 |
| Control Compound 1 | 30 |

Examples of the preparations of compounds according to the present invention are given below.

EXAMPLE 1

Preparation of N-(1-phenyl-3-piperidinopropyl)quinaldinamide by acid halide process To a solution of 655 mg (3.0 mmol) of 1-(3-amino-3-phenylpropyl)piperidine and 334 mg (3.3 mmol) of triethyamine in 3 ml of dichloromethane was dropwise added over a period of 20 min. under chilling with ice a solution of 575 mg (3.0 mmol.) of quinaldinoyl chloride in 6 ml of dichloromethane. After the addition was complete, the resulting mixture was stirred for 3 hours at room temperature, and to the mixture was added 30 ml of ether. The reaction mixture was washed twice with water and subsequently with a saturated aqueous sodium chloride solution and then dried over sodium sulfate. Thus dried mixture was evaporated under reduced pressure to remove the solvent. The residue was purified by silica gel column chromatography (silica gel: 6 g, CHCl$_3$ and CHCl$_3$/CH$_3$OH (50:1-20:1)) to obtain 1.06 g (yield: 95%) of the subject compound as a pale yellow crystalline product.

M.p.: 88°-90° C. (70% ethanol)

IR$\nu_{max}^{KBr}$(cm−1): 3230, 2930, 2850, 2780, 1665, 1560, 1510, 1485, 1445, 1420, 1155, 1145, 1115, 1105, 845, 750, 695.

NMR(CDCl$_3$)δ: 1.30-2.62(14H, m,

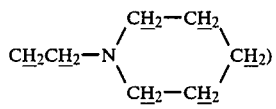

5.20-5.54(1H, m, CONHC$\underline{H}$) 70.4-8.36(11H, m, aromatic proton), 9.60(1H, broad d, CON$\underline{H}$).

EXAMPLE 2

Preparation of N-(1-phenyl-3-piperidinopropyl)quinaldinamide using condensation agent To a solution of 1.73 g (10 mmol.) of quinaldinic acid and 1.53 g (10 mmol.) of 1-hydroxybenzotriazole monohydrate in 50 ml of ethyl acetate was dropwise added over a period of 20 min. under chilling with ice a solution of 2.06 g (10 mmol.) of N,N'-dicyclohexylcarbodiimide in 10 ml of ethyl acetate. After the addition was complete, the resulting mixture was stirred for 2 hours at room temperature and chilled with ice. To the chilled mixture was dropwise added over a period of 30 min. a solution of 2.18 g (10 mmol.) of 1-(3-amino-3-phenyl-propyl)piperidine in 8 ml of ethyl acetate. After the addition was complete, the mixture was stirred overnight at room temperature. Precipitated insolubles were filtered off and then the insolubles were washed with ethyl acetate. The filtrate and the washings were combined and washed twice with a saturated aqueous sodium hydrogencarbonate solution and once with a saturated aqueous sodium chloride solution. The mixture was then dried over sodium sulfate, and was evaporated under reduced pressure to remove the solvent. The residue was crystallized after addition of n-hexane. The resulting crystals were washed three times with n-hexane and dissolved in 35 ml of ethyl acetate. The resulting solution was allowed to stand overnight in a refrigerator. Precipitated insolubles were filtered off and the insolubles were washed with ethyl acetate. The filtrate and the washings were combined and concentrated under reduced pressure. The residue was purified by silica gel column chromatography (silica gel: 40 g, CHCl$_3$ and CHCl$_3$/CH$_3$OH (30:1)) to obtain 3.07 g (yield: 82%) of the subject compound as a pale yellow crystalline product.

EXAMPLE 3

Preparation of N-(1-phenyl-3-piperidinopropyl)quinaldinamide using condensation agent To a suspension of 866 mg (5.0 mmol.) of quinaldinic acid and 576 mg (5.0 mmol.) of 1-hydroxysuccinimide in 20 ml of ethyl acetate was dropwise added over a period of 5-10 min. under chilling with ice a solution of 1.09 g (5.0 mmol.) of N,N'-dicyclohexylcarbodiimide. After the addition was complete, the mixture was stirred for 2 hours at room temperature. To this mixture was dropwise added a solution of 1.09 g (5.0 mmol.) of 1-(3-amino-3-phenylpropyl)piperidine in 5 ml of ethyl acetate. After the addition was complete, the mixture was stirred overnight at room temperature. Precipitated insolubles were filtered off and then the insolubles were washed with ethyl acetate. The filtrate and the washings were combined and washed twice with a saturated aqueous sodium hydrogencarbonate solution and once with a saturated aqueous sodium chloride solution. The mixture was then dried over sodium sulfate, and was evaporated under reduced pressure to remove the solvent. The residue was purified by silica gel column chromatography (silica gel: 20 g, CHCl$_3$ and CHCl$_3$/CH$_3$OH (30:1)) to obtain 1.72 g (yield: 92%) of the subject compound as a pale yellow crystalline product.

EXAMPLE 4

Preparation of N-(1-phenyl-3-piperidinopropyl)quinaldinamide by mixed acid anhydride process A solution of 520 mg (3.0 mmol.) of quinaldinic acid and 304 mg (3.0 mmol.) in dry tetrahydrofuran was chilled to −10°−−5° C. To the chilled solution (lower than −5° C.) was dropwise added 326 mg (3.0 mmol.) of ethyl chlorocarbonate. After 5 min., to the resulting mixture was dropwise added a solution of 655 mg (3.0 mmol.) of 1-(3-amino-3-phenylpropyl)piperidine in 6 ml of dry dichloromethane. The mixture was stirred at 0° C. for 1 hour and then stirred overnight at room temperature. The reaction mixture was concentrated under reduced pressure. The residue was violently shaken with a mixture of dichloromethane and 5% aqueous sodium hydroxide solution, and the organic layer was separated. The organic solution was washed successively with water and a saturated aqueous chloride solution and then dried over sodium sulfate. Thus dried solution was concentrated under reduced pressure. The residue was purified by silica gel column chromatography (silica gel: 15 g, CHCl$_3$ and CHCl$_3$/CH$_3$OH (30:1)) to obtain 1.10 g (yield: 98%) of the subject compound as a pale yellow crystalline product.

EXAMPLE 5

Preparation of N-(1-Phenyl-3-piperidinopropyl)quinaldinamide fumarate

To a solution of 3.02 g (8.1 mmol.) of N-(1-phenyl-3-piperidinopropyl)quinaldinamide in a mixture of 18 ml of ethanol and 8 ml of acetone was added a solution of 0.939 g (8.1 mmol.) of fumaric acid in 20 ml of hot ethanol. The resulting mixture was stirred at room temperature and subsequently under chilling with ice. Precipitated crystals were collected by filtration and washed with acetone. The washed crystals were suspended in 60 ml of n-hexane and the suspension was refluxed for 1.5 hours. The crystals were collected by filtration, washed with n-hexane and dried. Thus, 3.10 g (yield: 78%) of the subject compound was obtained as a white crystalline product.

M.p.: 164°–166° C.

IR$\nu_{max}^{KBr}$(cm$^{-1}$): 3400, 3250, 2950, 2870, 1710, 1670, 1590, 1515, 1490, 1445, 1420, 1350, 1300, 1250, 1190, 855, 780, 770, 700.

NMR(CDCl$_3$/CD$_3$OD=6/1)δ: 1.38–2.06(6H, m,

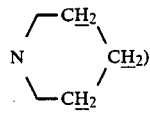

2.24–3.24(8H, m,

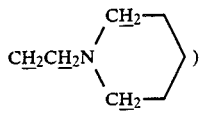

5.02–5.32(1H, m, CONHC$\underline{H}$), 6.77 (2H, s, C$\underline{H}$=C$\underline{H}$), 7.10–8.36(11H, m, aromatic proton).

EXAMPLE 6

Preparation of N-(1-phenyl-3-pyrrolidinopropyl)quinaldinamide

The procedure of Example 1 was repeated using 613 mg (3.0 mmol.) of 1-(3-amino-3-phenylpropyl)pyrrolidine and 575 mg (3.0 mmol.) of quinaldinoyl chloride, to obtain 1.08 g (yield: 100%) of the subject compound as a pale yellow crystalline product.

M.p.: 98°–99.5° C. (isopropyl alcohol).

IR$\nu_{max}^{KBr}$(cm$^{-1}$): 3240, 2930, 2790, 1665, 1555, 1510, 1485, 1450, 1420, 1205, 1160, 1140, 845, 750, 700.

NMR(CDCl$_3$)δ: 1.60–2.77(12H, m,

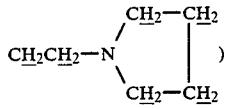

5.22–5.57(1H, m, CONHC$\underline{H}$), 7.14–8.39(11H, m, aromatic proton), 9.55(1H, broad d, CON$\underline{H}$).

EXAMPLE 7

Preparation of N-(1-phenyl-3-pyrrolidinopropyl)quinaldinamide oxalate

In ethanol were dissolved 259 mg (0.72 mmol.) of N-(1-phenyl-3-pyrrolidinopropyl)quinaldinamide and 91 mg of oxalic acid dihydrate. The resulting solution was evaporated under reduced pressure to remove the solvent. The residue was recrystallized from a mixture of acetone (6 ml) and diethyl ether (3 ml) to obtain 310 mg (yield: 96%) of the subject compound as a white crystalline product.

M.p.: 138°–140° C.

IR$\nu_{max}^{KBr}$(cm$^{-1}$): 3380, 3300, 3040, 1725, 1660, 1560, 1520, 1490, 1425, 1210, 840, 770, 695.

NMR(CDCl$_3$)δ: 1.82–2.26(4H, m,

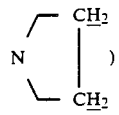

2.30–2.70(2H, m,

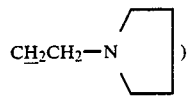

2.81–3.73(6H, m,

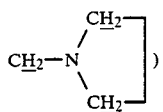

5.00–5.39(1H, m, CONHC$\underline{H}$), 7.11–8.38(11H, m, aromatic proton), 8.67(1H, broad d, CON$\underline{H}$).

EXAMPLE 8

Preparation of N-[3-(1-perhydroazepin-1-yl)-1-phenylpropyl]quinaldinamide

The procedure of Example 1 was repeated using 697 mg (3.0 mmol.) of 1-(3-amino-3-phenylpropyl)perhydroazepine and 575 mg (3.0 mmol.) of quinaldinoyl chloride, to obtain 921 mg (yield: 79%) of the subject compound as a pale yellow oily product.

IR$\nu_{max}^{neat}$(cm$^{-1}$): 3390, 3300, 2930, 2860, 2820, 1670, 1565, 1515, 1495, 1450, 1415, 1145, 845, 775, 750, 700.

NMR(CDCl$_3$)δ: 1.30–2.84(16H, m,

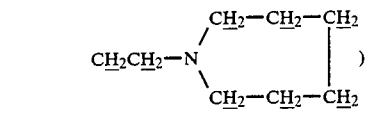

5.17–5.50(1H, m, CONHC$\underline{H}$), 7.02–8.38(11H, m, aromatic proton), 9.40(1H, broad d, CON$\underline{H}$).

EXAMPLE 9

Preparation of N-[3-(1-perhydroazepin-1-yl)-1-phenylpropyl]quinaldinamide oxalate In ethanol were dissolved 921 mg (2.38 mmol.) of N-[3-(perhydroazepin-1-yl)-1-phenylpropyl]quinaldinamide and 300 mg (2.38 mmol.) of oxalic acid dihydrate. The resulting solution was evaporated under reduced pressure to remove the solvent. The residue was recrystallized from a mixture of ethanol (10 ml) and n-hexane (10 ml) to obtain 920 mg (yield: 81%) of the subject compound as a white crystalline product.

M.p.: 149°–151° C.

IR$\nu_{max}^{KBr}$(cm$^{-1}$): 3440, 3350, 2940, 2860, 1720, 1670, 1630, 1560, 1520, 1490, 1450, 1420, 1400, 1180, 845, 770, 690.

NMR(CDCl$_3$)δ: 1.44–2.05(8H, m,

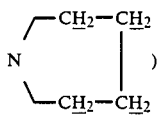

2.30–2.70(2H, m,

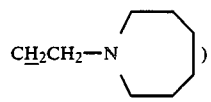

2.90–3.46(6H, m,

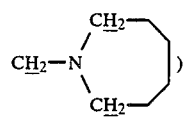

4.99–5.34(1H, m, CONHCH), 7.10–8.34(11H, m, aromatic proton), 8.70(1H, broad d, CONH).

EXAMPLE 10

Preparation of N-(3-diethylamino-1-phenylpropyl)quinaldinamide

The procedure of Example 1 was repeated using 618 mg (3.0 mmol.) of N-(3-amino-3-phenylpropyl)-N,N-diethylamine and 575 mg (3.0 mmol.) of quinaldinoyl chloride, to obtain 1.08 g (yield: 100%) of the subject compound as a pale yellow oily product.

IR$\nu_{max}^{neat}$(cm$^{-1}$): 3380, 3220, 2970, 2810, 1670, 1565, 1510, 1490, 1425, 1210, 1160, 1145, 1070, 845, 750, 695.

NMR(CDCl$_3$)δ: 1.06(6H, t, J=7 Hz, N(CH$_2$CH$_3$)$_2$), 1.84–2.90(8H, m, CH$_2$CH$_2$N(CH$_2$CH$_3$)$_2$), 5.17–5.50(1H, m, CONHCH), 7.12–8.38(11H, m, aromatic proton).

EXAMPLE 11

Preparation of N-(3-diethylamino-1-phenylpropyl)quinaldinamide fumarate

In ethanol were dissolved under heating 1.08 g (3.0 mmol.) of N-(3-diethylamino-1-phenylpropyl)quinaldinamide and 313 mg (3.0 mmol.) of fumaric acid. The resulting solution was evaporated under reduced pressure to remove the solvent. The residue was recrystallized from 8 ml of ethanol to obtain 1.14 g (yield: 88%) of the subject compound as a white crystalline product.

M.p.: 160°–161° C.

IR$\nu_{max}^{KBr}$(cm$^{-1}$): 3280, 2990, 2950, 1655, 1560, 1520, 1495, 1425, 1210, 1160, 980, 845, 775, 750, 695.

NMR(CDCl$_3$/CD$_3$OD=6/1)δ: 1.24(6H, t, J=7 Hz, N(CH$_2$CH$_3$)$_2$), 2.20–2.70(2H, m, CH$_2$CH$_2$N(CH$_2$CH$_3$)$_2$), 2.80–3.40(6H, m, CH$_2$N(CH$_2$CH$_3$)$_2$), 5.06–5.34(1H, m, CONHCH), 6.76 (2H, s, CH=CH), 7.20–8.38(11H, m, aromatic proton).

EXAMPLE 12

Preparation of N-[1-(2-methylphenyl)-3-piperidinopropyl]quinaldinamide

The procedure of Example 4 was repeated using 465 mg (2.0 mmol.) of 1-[3-amino-3-(2-methylphenyl)propyl]piperidine and 347 mg (2.0 mmol.) of quinaldinic acid, to obtain 736 mg (yield: 95%) of the subject compound as a pale yellow oily product.

IR$\nu_{max}^{neat}$(cm$^{-1}$): 3260, 2930, 2850, 2800, 2770, 1665, 1515, 1495, 1425, 1160, 850, 755.

NMR(CDCl$_3$)δ: 1.28–1.88(6H, m,

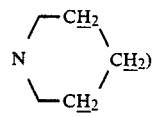

1.88–2.60(8H, m,

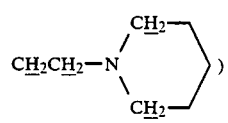

2.49 (3H, s, CH$_3$), 5.36–5.68(1H, m, CONHCH), 6.90–8.30(10H, m, aromatic proton), 9.48(1H, broad d, CONH).

EXAMPLE 13

Preparation N-[1-(2-methylphenyl)-3-piperidinopropyl]quinaldinamide fumarate

The procedure of Example 11 was repeated using 736 mg (1.9 mmol.) of N-[1-(2-methylphenyl)-3-piperidinopropyl]quinaldinamide and 220 mg (1.9 mmol.) of fumaric acid, to obtain 708 mg (yield: 74%) of the subject compound.

IR$\nu_{max}^{KBr}$(cm$^{-1}$): 3420, 3320, 2950, 1670, 1625, 1510, 1490, 1440, 1300, 1280, 1200, 770, 750.

NMR(CDCl$_3$/CD$_3$OD=2/1)δ: 1.42–2.04(6H, m,

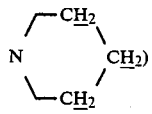

2.20–2.68(2H, m,

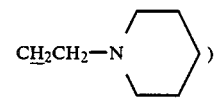

2.45 (3H, s, CH$_3$), 2.88–3.26(6H, m,

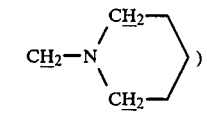

5.24–5.56(1H, m, CONHCH), 6.75 (2H, s, CH=CH), 7.04–8.40(10H, m, aromatic proton).

EXAMPLE 14

Preparation of N-[1-(3-methylphenyl)-3-piperidinopropyl]quinaldinamide

The procedure of Example 1 was repeated using 697 mg (3.0 mmol.) of 1-[3-amino-3-(3-methylphenyl)- propyl]piperidine and 575 mg (3.0 mmol.) of quinaldinoyl chloride, to obtain 755 mg (yield: 65%) of the subject compound as a pale yellow solid product.

IR$\nu_{max}^{KBr}$(cm$^{-1}$): 3250, 2930, 2850, 2790, 1665, 1560, 1510, 1490, 1420, 1160, 1125, 845, 790, 750, 710.

NMR(CDCl$_3$)δ: 1.35–2.60(17H, m,

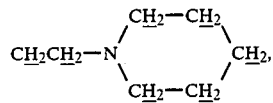

CH$_3$), 5.17–5.48(1H, m, CONHCH), 6.90–8.35(10H, m, aromatic proton), 9.50(1H, broad d, CONH).

EXAMPLE 15

Preparation of N-[1-(3-methylphenyl)-3-piperidinopropyl]quinaldinamide fumarate

The procedure of Example 11 was repeated using 678 mg (1.75 mmol.) of N-[1-(3-methylphenyl)-3-piperidinopropyl]quinaldinamide and 203 mg (1.75 mmol.) of fumaric acid, to obtain 620 mg (yield: 70%) of the subject compound as a white crystalline product.

M.p.: 143°–145° C.

IR$\nu_{max}^{KBr}$(cm$^{-1}$): 3460, 3340, 3020, 2950, 2860, 1670, 1560, 1520, 1490, 1420, 1290, 1165, 980, 840, 770, 700.

NMR(CDCl$_3$/CD$_3$OD=6/1)δ: 1.40–2.00(6H, m,

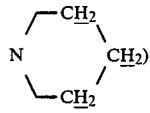

2.20–2.65(5H, m,

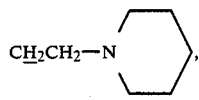

CH$_3$) 2.80–3.20(6H, m,

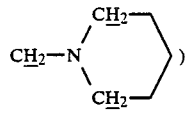

5.00–5.27(1H, m, CONHCH), 6.76 (2H, s, CH=CH), 6.94–8.37(10H, m, aromatic proton).

EXAMPLE 16

Preparation of N-[1-(4-methylphenyl)-3-piperidinopropyl]quinaldinamide

The procedure of Example 1 was repeated using 697 mg (3.0 mmol.) of 1-[3-amino-3-(4-methylphenyl)-propyl]piperidine and 575 mg (3.0 mmol.) of quinaldinoyl chloride, to obtain 1.09 g (yield: 94%) of the subject compound as a pale yellow oily product.

IR$\nu_{max}^{neat}$(cm$^{-1}$): 3390, 3280, 2940, 2870, 2810, 1670, 1565, 1510, 1490, 1425, 1160, 1125, 850, 815, 795, 760.

NMR(CDCl$_3$)δ: 1.35–2.60(17H, m,

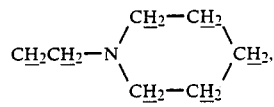

CH$_3$), 5.16–5.45(1H, m, CONHCH), 6.95–8.34(10H, m, aromatic proton), 9.50(1H, broad d, CONH).

EXAMPLE 17

Preparation of N-[1-(4-methylphenyl)-3-piperidinopropyl]quinaldinamide oxalate

The procedure of Example 7 was repeated using 917 mg (2.36 mmol.) of N-[1-(4-methylphenyl)-3-piperidinopropyl]quinaldinamide and 298 mg (2.36 mmol.) of oxalic acid dihydrate, to obtain 901 mg (yield: 80%) of the subject compound as a whilte crystalline product upon recrystallization from 8 ml of ethanol.

M.p.: 165°–167° C. (decomp.).

IR$\nu_{max}^{KBr}$(cm$^{-1}$): 3440, 3370, 3010, 2940, 2860, 1720, 1680, 1560, 1510, 1490, 1420, 1200, 1155, 835, 800, 790, 765.

NMR(CDCl$_3$/CD$_3$OD=6/1)δ: 1.40–2.05(6H, m,

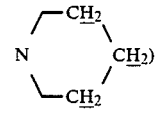

2.24–2.66(5H, m,

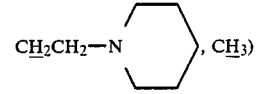

2.70–3.40(6H, m,

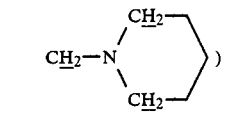

5.00–5.27(1H, m, CONHCH), 7.05–8.38(10H, m, aromatic proton).

EXAMPLE 18

Preparation of N-[1-(4-methoxyphenyl)-3-piperidinopropyl]quinaldinamide

The procedure of Example 1 was repeated using 745 mg (3.0 mmol.) of 1-[3-amino-3-(4-methoxyphenyl)-propyl]piperidine and 575 mg (3.0 mmol.) of quinaldinoyl chloride, to obtain 1.03 g (yield: 85%) of the subject compound as a pale yellow oily product.

IR$\nu_{max}^{neat}$(cm$^{-1}$): 3380, 3260, 3000, 2930, 2850, 2820, 2800, 2760, 1665, 1610, 1560, 1510, 1490, 1420, 1245, 1175, 1155, 1120, 1030, 840, 820, 790, 750.

NMR(CDCl$_3$)δ: 1.34–2.60(14H, m,

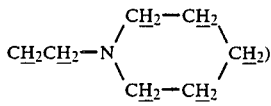

3.75 (3H, s, OC$\underline{H}_3$), 5.18–5.46(1H, m, CONHC$\underline{H}$), 6.72–8.34(10H, m, aromatic proton), 9.50(1H, broad d, CON$\underline{H}$).

EXAMPLE 19

Preparation of N-[1-(4-methoxyphenyl)-3-piperidinopropyl]quinaldinamide oxalate The procedure of Example 7 was repeated using 1.03 g (2.56 mmol.) of N-[1-(4-methoxyphenyl)-3-piperidinopropyl]quinaldinamide and 323 mg (2.56 mmol.) of oxalic acid dihydrate, to obtain 884 mg (yield: 70%) of the subject compound as a white powdery product upon recrystallization from 8 ml of ethanol.

IR$\nu_{max}^{KBr}$(cm$^{-1}$): 3440, 3370, 2940, 1720, 1660, 1610, 1560, 1510, 1490, 1420, 1245, 1180, 1030, 845, 825, 775.
NMR(CDCl$_3$)$\delta$: 1.38–2.16(6H, m,

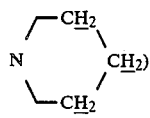

2.16–3.85(11H, m,

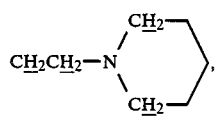

OC$\underline{H}_3$), 4.92–5.26(1H, m, CONHC$\underline{H}$), 6.68–8.26(10H, m, aromatic proton), 8.50 (1H, broad d, CON$\underline{H}$).

REFERENCE EXAMPLE 1

Preparation of β-piperidinopropiophenone hydrochloride

A mixture of 120 g of acetophenone, 133 g of piperidine hydrochloride and 50 g of paraformaldehyde in 120 ml of ethanol was refluxed for 6 hours. The mixture was then allowed to stand for cooling to soldify. The resulting solid was crushed after addition of 400 ml of acetone, and then collected by filtration. The collected solid was washed successively with acetone and hexane and dried to obtain 191.6 g (yield: 75.4%) of the subject compound as a white scaly product.

In the same manner as above, the following compounds were obtained.

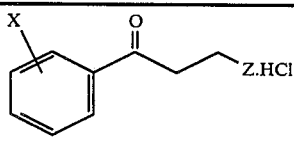

| | | |
|---|---|---|
| X = H, 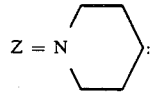 Z = N⟨piperidine⟩ | | m.p. 189–190° C. |

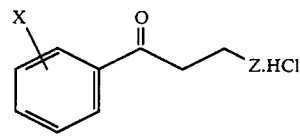

| X | Z | m.p. |
|---|---|---|
| X = H, | 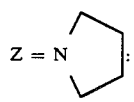 Z = N⟨pyrrolidine⟩ | m.p. 160–162° C. |
| X = H, | 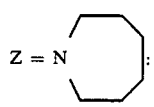 Z = N⟨azepane⟩ | m.p. 160–161.5° C. |
| X = H, | Z = N(C$_2$H$_5$)$_2$ | m.p. 92–93° C. |
| X = o-CH$_3$, | 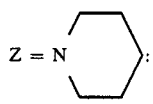 Z = N⟨piperidine⟩ | m.p. 170–172° C. |
| X = m-CH$_3$, | 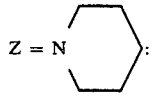 Z = N⟨piperidine⟩ | m.p. 154–155° C. |
| X = p-CH$_3$, | 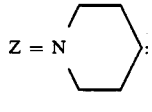 Z = N⟨piperidine⟩ | m.p. 173–175° C. |
| X = p-OCH$_3$, | 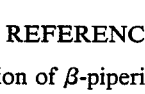 Z = N⟨piperidine⟩ | m.p. 205–207° C. (decomp.) |

REFERENCE EXAMPLE 2

Preparation of β-piperidinopropiophenone oxime

In 470 ml of water were dissolved 60.2 g of β-piperidinopropiophenone hydrochloride and 18.1 g of hydroxylamine hydrochloride. To this solution was added portionwise 21.9 g of sodium hydrogencarbonate. After the whole amount was added, the mixture was stirred overnight. To the stirred mixture was then added an aqueous solution of 14.2 g of sodium hydroxide in 47 ml of water. Thus obtained mixture was well stirred and allowed to stand for 2 hours to produce a white precipitate. The precipitate was collected by filtration and washed successively with two portions of 200 ml of water and ethanol. The washed precipitate was dried to obtain a white solid. The solid was then recrystallized from methanol to obtain 41.2 g (yield: 74.8%) of the subject compound as a silver-white scaly product.

In the same manner as above, the following compounds were obtained.

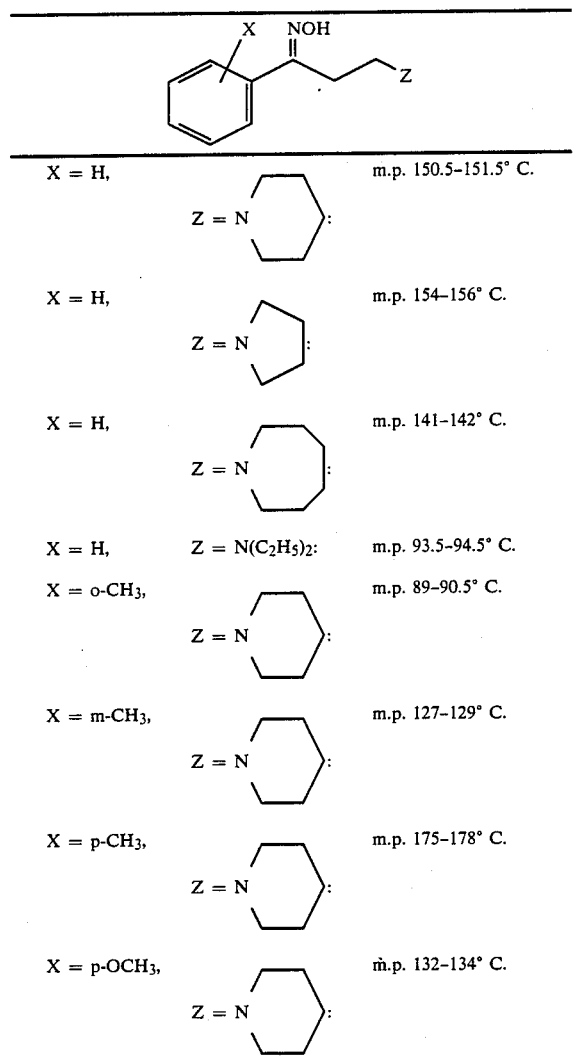

REFERENCE EXAMPLE 3

Preparation of 1-(3-amino-3-phenylpropyl)piperidine dioxalate

To a stirred solution of 23.2 g of β-piperidinopropiophenone oxime in 200 ml of formic acid was added portionwise 19.6 g of zinc powder. The resulting mixture generated heat to elevate its temperature. When the temperature of the mixture reached 65° C., the addition was interrupted. Thereafter, the addition of zinc powder was continued intermittently to keep the mixture at a temperature within 60° to 65° C. When it was observed that the addition of zinc powder caused no generation of heat, the whole portion of the remaining zinc powder was added to the reaction mixture. The mixture was subsequently stirred for 2 hours. The insolubles were filtered off and washed with 100 ml of formic acid. The filtrate and the washings were combined together and concentrated under reduced pressure. To the residue was added 200 ml of water. The resulting aqueous solution was adjusted to pH 8 by addition of aqueous sodium hydroxide solution and washed with chloroform. The aqueous solution was then made to pH 11 by addition of aqueous sodium hydroxide solution and extracted with chloroform. The extract was dried over sodium sulfate. The dried extract was evaporated under reduced pressure to remove the solvent. Thus, a crude base product of the subject compound was obtained.

The crude product was dissolved in 200 ml of ethanol, and to this solution was added a solution of 25.2 g of oxalic acid dihydrate in 200 ml of ethanol. The mixture was allowed to stand to produce white crystals. The crystals were collected by filtration, washed with ethanol and dried to obtain 27.9 g (yield: 70%) of the subject compound.

In the same manner as above, the following compounds were obtained.

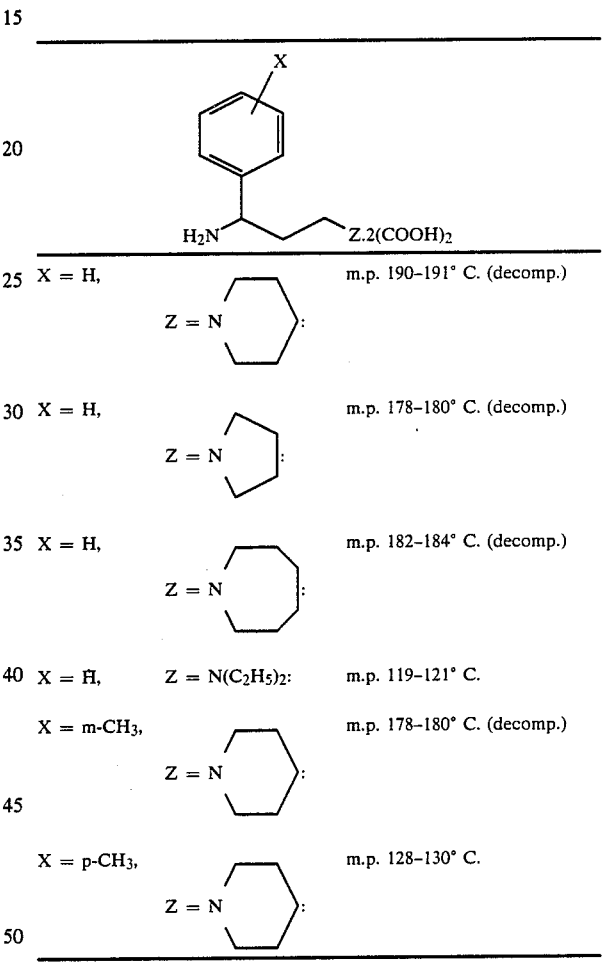

The dioxalates can be converted to free acids by treatment with an aqueous alkaline solution.

EXAMPLE 20

Preparation in the form of pellet

A pellet (220 mg) containing:

| | |
|---|---|
| quinaldinamide compound (active component) | 50 mg |
| lactose | 103 mg |
| starch | 50 mg |
| magnesium stearate | 2 mg |
| hydroxypropylcellulose | 15 mg | was obtained.

EXAMPLE 21

Preparation in the form of capsule

A gelatin-shell hard capsule containing 350 mg of the core portion consisting of:

| | |
|---|---|
| quinaldinamide compound (active component) | 40 mg |
| lactose | 200 mg |
| starch | 70 mg |
| polyvinylpyrrolidone | 5 mg |
| crystalline celllulose | 35 mg | was obtained.

EXAMPLE 22

Preparation in the form of granules

One gram of granules containing:

| | |
|---|---|
| quinaldinamide compound (active component) | 200 mg |
| lactose | 450 mg |
| corn starch | 300 mg |
| hydroxypropylcellulose | 50 mg | was obtained.

We claim:

1. A quinaldinamide derivative having the formula (I):

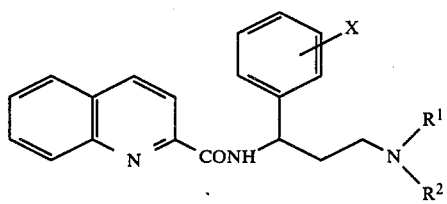

(I)

wherein
each of $R^1$ and $R^2$ independently represents a lower alkyl group or $R^1$ and $R^2$ are an alkylene which combined together with the adjacent nitrogen atom to form a 5-7 membered ring; and
X represents the hydrogen atom, a lower alkyl group or a lower alkoxy group.
and its pharmaceutically acceptable acid-addition salt.

2. The quinaldinamide derivative of the formula (I) and its pharmaceutically acceptable acid-addition salt as claimed in claim 1, wherein each of $R^1$ and $R^2$ independently represents an alkyl group containing 1-6 carbon atoms.

3. The quinaldinamide derivative of the formula (I) and its pharmaceutically acceptable acid addition salt as claimed in claim 1, wherein $R^1$ and $R^2$ are combined together with the adjacent nitrogen atom to form a 5-7 membered ring.

4. The quinaldinamide derivative of the formula (I) and its pharmaceutically acceptable acid addition salt as claimed in claim 1, wherein X represents the hydrogen atom.

5. The quinaldinamide derivative of the formula (I) and its pharmaceutically acceptable acid addition salt as claimed in claim 1, wherein X represents a lower alkyl group containing 1-6 carbon atoms.

6. The quinaldinamide derivative of the formula (I) and its pharmaceutically acceptable acid addition salt as claimed in claim 1, wherein X represents a lower alkyl group or a lower alkoxy group containing 1-6 carbon atoms.

7. The quinaldinamide derivative of the formula (I) and its pharmaceutically acceptable acid addition salt as claimed in claim 1, wherein the quinaldinamide derivative is N-(3-dimethylamino-1-phenylpropyl)quinaldinamide, N-(3-diethylamino-1-phenylpropyl)quinaldinamide, N-(1-phenyl-3-dipropylaminoproyl)quinaldinamide, N-(1-phenyl-3-pyrrolidinopropyl)quinaldinamide, N-(1-phenyl-3-piperidinopropyl)quinaldinamide, N-[3-(perhydroazepin-1-yl)-1-phenylpropyl]quinaldinamide, N-[1-(2-methylphenyl-3-piperidinopropyl]quinaldinamide, N-[1-(3-methylphenyl)-3-piperidinopropyl]quinaldinamide, N-[1-(4-methylphenyl)-3-piperidinopropyl]quinaldinamide or N-[1-(4-methoxyphenyl)-3-piperidinopropyl]quinaldinamide.

8. The pharmaceutically acceptable acid addition salt of the quinaldinamide derivative of the formula (I) as claimed in claim 1, wherein the acid is hydrochloric acid, hydrobromic acid, sulfuric acid, phosphoric acid, citric acid, fumaric acid, maleic acid, tartaric acid, oxalic acid, methanesulfonic acid or p-toluenesulfonic acid.

* * * * *